| United States Patent [19] | [11] Patent Number: 4,902,850 |
| Davis | [45] Date of Patent: Feb. 20, 1990 |

[54] PURIFICATION OF ANETHOLE BY CRYSTALLIZATION

[75] Inventor: Curry B. Davis, Panama City, Fla.

[73] Assignee: Arizona Chemical Company, Panama City, Fla.

[21] Appl. No.: 229,004

[22] Filed: Aug. 5, 1988

[51] Int. Cl.⁴ .............................................. C07C 7/14
[52] U.S. Cl. .................................... 585/817; 568/658; 208/39
[58] Field of Search .................... 208/39, 29; 585/812, 585/816–817; 568/658

[56] References Cited

U.S. PATENT DOCUMENTS

| 1,777,704 | 10/1930 | Smith | 508/650 |
| 1,928,020 | 9/1933 | Humphrey | 568/658 X |
| 1,977,064 | 10/1934 | Humphrey | 568/658 X |
| 2,013,619 | 9/1935 | Angstadt | 208/39 |
| 2,815,364 | 12/1957 | Green | 585/812 X |
| 3,038,945 | 6/1982 | Garber et al. | 568/658 |

OTHER PUBLICATIONS

"Anethole Production, Properties and Uses", Wagner, Manufacturing Chemist, Feb. 1952, pp. 56–59.

*Primary Examiner*—Glenn Caldarola
*Attorney, Agent, or Firm*—Luedeka, Hodges & Neely

[57] ABSTRACT

A method of purification for anethole which involves forming an aqueous emulsion of crude anethole and crystallizing anethole from the emulsion. The process provides a purified anethole having improved odor and taste.

5 Claims, No Drawings

PURIFICATION OF ANETHOLE BY CRYSTALLIZATION

The present invention relates to a process for purifying crude anethole.

Anethole is used as a flavoring agent and it is essential that it has satisfactory organoleptic properties. The crude anethole contained in the high boiling fractions or residue from the distillation of crude wood, gum, and sulfate turpentines includes a variety of impurities (e.g. cis-anethole, and carophylenes, $C_{15}H_{24}$) which adversely affects the taste and odor of the product. In addition, crude anetholes derived from sulfate turpentines contain substantial amounts of sulfur-bearing impurities which result in serious taste and odor problems. To produce an organoleptically acceptable anethole virtually all of these impurities must be removed or substantially reduced in concentration (i.e. <0.5% total impurities).

Attempts have been made to deodorize and improve the taste of turpentine crude anethole distillates (a) by oxidizing the sulfide contaminants to sulfones or sulfoxides, (b) by steam distilling the distillate, (c) by multiple solvent crystallization, (d) by careful fractional distillation, (e) by liquid-liquid extraction, (f) by azeotropic fractional distillation, or (g) by combinations of versions of the foregoing methods. Each of these methods has certain difficulties and each is generally costly. None alone gives a high yields of a first quality anethole (taste/odor). However, various combinations of the methods can result in the preparation of a high quality anethole.

Attempts to "sweeten" or deodorize and improve the taste of the distillate involve oxidizing the sulfides contained therein to sulfones or sulfoxides by treatment with aqueous hypochlorite. The odor of the distillate is improved somewhat by this treatment, but organic chlorides are introduced as contaminants. The organic chlorides are malodorous, corrosive, and may lead to adverse physiological side effects. Sweetening the distillate by treatment with organic peracids, as set forth in U.S. Patent No. 3,909,395 to Takacs on September 30, 1975, avoids the problems encountered in the treatment with aqueous hypochlorite. The peracid treatment preferably is used in conjunction with steam distillation in order to produce acceptably low sulfur concentrations of about 100 ppm or less in the final product. This method does not reduce the cis-anethole content.

Steam distillation at atmospheric pressure with liquid water present does not remove or separate low boiling sulfur components in general. It is more effective if the sulfur impurities are polar as they are if they are oxidized before steam distillation.

The use of multiple solvent crystallization as a means of increasing the purity of anethole has major drawbacks. The first problem, is that the net recovery is low after the three or four crystallizations necessary to achieve satisfactory purity. Multiple crystallization out of solvent also requires progressively lower temperatures if the mother liquor fractions are reprocessed. There is the added problem of dealing with the solvent used in the crystallizations. These problems combine to result in a product that is very expensive to prepare.

In short, non of the above methods is entirely satisfactory.

The overall objective is to produce a high purity trans-anethole which is most critically defined by its sulfur content. In addition, the cis-anethole content must be below 0.1% to have an excellent taste. High purity is required to give the desired taste and odor, which is characterized as being licorice or anise seed like. Other objects and advantages will become apparent to one skilled in the art from the following description.

In general, the process involves increasing the purity of anethole by first preparing the aqueous emulsion. The percent anethole in the emulsion can vary depending on convenience. The emulsion is then cooled to below the crystallization point and preferably to about 0° C. to crystallize the anethole. Sub zero temperatures (<0° C.) could be used if an antifreeze such as methanol is used to depress the freezing point of water. After crystallization is completed, the crystals are separated from the aqueous emulsion. The crystals of purified anethole are further purified by reslurrying them with cold water and an emulsifier or surfactant (the crystals of purified anethole are substantially insoluble in cold water), after which they are again separated from the wash water. The preceding step may be repeated several times if desired.

To remove residual water from the final product, the crystals are melted and the water separated at approximately 25°–50° C. from the liquid anethole. This highly purified anethole has a much reduced concentration of sulfur contaminants and excellent odor and taste.

In order to facilitate a further understanding of the invention, the following examples are given primarily for purposes of illustrating certain more specific details thereof. Unless otherwise noted, the parts are by weight.

EXAMPLE 1

Crude anethole (87% pure) is recovered from crude suflate turpentine by means of a series of fractional distillations. An emulsion of this crude anethole is prepared by combining 150 parts of the anethole, three parts of the potassium soap of tall oil fatty acid and 375 parts of water at a temperature above the melting point of anethole. The pH is adjusted to 9.5 with potassium hydroxide and the mixture is agitated in a high speed (10,000 rpm) mixer. An oil in water emulsion results. The anethole emulsion has a low viscosity and contains 28.6% organic solids.

The anethole emulsion (525 parts) is charged into a one liter, three neck flask containing a stirrer. The flask is provided with a bottom drain covered with a 4 cm diameter 100 mesh inert metal screen. The flask is supported in a temperature controlled water bath. With mild agitation, the emulsion is cooled rapidly to about 10° C. and then slowly to about 0° C. (in this example about four hours). If the cooling is too rapid, particularly in the region of 6° C. to 8° C., the crystallizing mass becomes too viscous to maintain good mixing and temperature control. After holding the mixture one hour at 0° C., the bottom drain is opened and mild vacuum is applied to remove the liquid phase.

The crystals which remain in the flask are then reslurried and refiltered three times with 375 ml portions of ice water (0°–3° C.) containing 0.1 part of the potassium soap. The filtrates are combined with the original mother liquor for later recovery.

The purified final product is obtained by melting the crystals at 50° C. and separating the residual water. The table below shows the quality of the produced.

|  | Crude | Product |
|---|---|---|
| trans-Anethole Content, % by Gas Liquid Chromatography | 87 | 99.6 |
| Sesquiterpenes and Other Impurities, % | 12 | 0.1 |
| Sulfur, ppm | 4800 | 100 |
| cis-Anethole Content, % | 1.1 | 0.3 |
| Congealing Temperature, °C. | 14 | 21.2 |
| Net Yield |  | 78%* |

*This represents 68 parts of trans-anethole out of 87 in the original crude or 78% yield of the contained anethole. The product had good taste and odor.

EXAMPLE 2

The method of Example 1 was applied to a higher quality crude with the following results:

|  | Crude | Product |
|---|---|---|
| trans-Anethole Content, % | 97 | 99.6 |
| Sesquiterpenes and Other Impurities, % | 2 | .2 |
| Sulfur, ppm | 250 | 10 |
| cis-Anethole, % | .5 | 0.1 |
| Congealing Temperature, °C. | 20.5 | 21.4 |
| Net Yield |  | 92% |

The product had excellent odor and taste.

EXAMPLE 3

A sample of anethole crude (same as Example 1) was steam distilled. (Atmospheric pressure conditions at 100° C.). The composition of the distillate, obtained in 85% yield, was:

|  | Crude | Product |
|---|---|---|
| trans-Anethole Content, % | 87 | 89 |
| cis-Anethole Content, % | 0.5 | 0.5 |
| Sulfur Content, ppm | 4800 | 4300 |

The results of this example show the minimum removal of sulfur by steam. The level of cis-anethole was not affected. The product had poor taste and odor.

EXAMPLE 4

An anethole of high purity (95%) was isolated from crude sulfate turpentine high boiling residue. This material was distilled to fractionate under the following conditions: 100 mm Hg./Reflux Ratio 10/1 20 theoretical plate column.

|  | Sulfur ppm | Yield % |
|---|---|---|
| Anethole Feed | 3870 |  |
| Low Boiling Fraction (155–160° C.) | 3310 | 8 |
| Product Cut (160–164° C.) | 3410 | 67 |
| Residue | 4470 | 22 |
| Loss | — | 3 |

Again there was poor sulfur removal and taste and odor were poor.

EXAMPLE 5

A sample of 100 parts of anethole was recrystallized from 100 parts of absolute ethanol by dissolving hot and then slowly cooling to 5° C. The yield of anethole was 60 parts and had the composition shown below:

|  | Feed USP Anethole | Recrystallized Anethole |
|---|---|---|
| trans-Anethole, % | 97.5 | 98 |
| Sulfur, ppm | 160 | 82 |
| Net Yield, % |  | 60 |

The produce had a good taste and odor but the yield was low. Compare, however, with Example 2 where a crude anethole of similar purity was purified by the process disclosed herein.

In the preferred embodiment of the invention, the emulsifier used is either a potassium or sodium soap of tall oil fatty acid. With anionic emulsifiers such as these the residual organics in the liquid aqueous phase that is removed may be recovered by acidification followed by separation. For purposes of purification of the anethole, however, either nonionic, anionic, or cationic emulsifiers may be employed.

The purity of product of the process is high with a very low concentration of sulfur contaminants. The purity of a starting crude anethole, with 87% anethole and 4800 ppm sulfur, is improved to 99.6% anethole with a sulfur contamination of only 100 ppm. In addition to a high purity product, the recovery rate of the anethole contained in the crude anethole is high using a relatively high crystallization temperature (i.e., 0° C. vs. −20° or −30° for solvent crystallization).

As a result, the invention provides a simple, economical, and effective method for reducing the concentrations of cis-anethole impurities as well as the concentration of sulfur-containing impurities from crude anethole. The product has high purity and is produced with good recovery. Further advantages arise from the absence of flammable solvents which can present a fire hazard. There is also less potential for contamination of a food grade product.

Various of the features of the invention which are believed to be novel are set forth in the appended claims.

What is claimed is:

1. The method of improving the purity of crude anethole from the residue or high boiling fractions from the distillation of crude wood, gum or sulfate turpentine comprising:
   preparing an aqueous emulsion of crude anethole by combining crude anethole, emulsifier, and water at a temperature above the melting point of the crude anethole and agitating the mixture;
   cooling the emulsion to form crystals of purified anethole;
   separating the anethole crystals from the aqueous emulsion liquid phase;
   washing the crystals of the purified anethole with cool water; and
   removing the residual water from the purified anethole.

2. The method of claim 1 wherein the crude anethole is derived from crude sulfate turpentine.

3. The method of claim 1 wherein the emulsifier is an alkali soap of tall oil fatty acid wherein the alkali is selected from the group consisting of potassium and sodium.

4. The method of claim 1 wherein the step of removing the residual water from the purified anethole further comprises:

melting the crystals of the purified anethole; and separating the residual water from the melted purified anethole.

5. The method of claim 1 wherein the emulsion is cooled rapidly to about 10° C. and then cooled slowly to about 0° C. under agitation to prevent abnormal increases in viscosity.

* * * * *